United States Patent [19]

Green et al.

[11] Patent Number: 5,376,101
[45] Date of Patent: Dec. 27, 1994

[54] SUTURE RETAINING CLIP

[75] Inventors: David T. Green, Westport; Henry Bolanos, East Norwalk; Henry R. Sienkiewicz, Stamford, all of Conn.; Kenneth E. Toso, Portchester, N.Y.; Michael S. Kolesa, Norwalk; H. Jonathan Tovey, Milford, both of Conn.

[73] Assignee: The United States Surgical Corporation, Norwalk, Conn.

[21] Appl. No.: 173,904

[22] Filed: Dec. 27, 1993

Related U.S. Application Data

[62] Division of Ser. No. 959,182, Oct. 9, 1992.

[51] Int. Cl.⁵ .............................................. A61B 17/04
[52] U.S. Cl. ...................................... 606/232; 606/151
[58] Field of Search ............... 606/120, 151, 157, 158, 606/232; D 24/27; D 8/395; 24/129 R, 132 R, 134 R, 306, 518, 521, 543, 457, 115 G, 73 P

[56] References Cited

U.S. PATENT DOCUMENTS

| | | |
|---|---|---|
| D. 190,787 | 6/1961 | Schneider . |
| D. 234,204 | 1/1975 | Miller et al. . |
| 600,887 | 3/1898 | Pettit . |
| 1,387,358 | 8/1921 | Castello ............... 24/115 G |
| 3,698,681 | 10/1972 | Lacey . |
| 3,753,438 | 8/1973 | Wood et al. . |
| 3,803,670 | 4/1974 | Johnson ................... 24/73 P |
| 3,854,482 | 12/1974 | Laugherty et al. . |
| 3,857,396 | 12/1974 | Hardwick . |
| 3,896,527 | 7/1975 | Miller et al. . |
| 3,910,281 | 10/1975 | Kletschka et al. . |
| 3,976,079 | 8/1976 | Samuels et al. . |
| 4,291,698 | 9/1981 | Fuchs et al. ............ 606/232 |
| 4,382,453 | 5/1983 | Bujan et al. . |
| 4,387,489 | 6/1983 | Dudek . |
| 4,492,232 | 1/1985 | Green . |
| 4,498,476 | 2/1985 | Cerwin et al. . |
| 4,519,392 | 5/1985 | Lingua . |
| 4,536,924 | 8/1985 | Willoughby . |
| 4,556,058 | 12/1985 | Green . |
| 4,557,263 | 12/1985 | Green . |
| 4,569,346 | 2/1986 | Poirier . |
| 4,620,541 | 11/1986 | Gertzman et al. . |
| 4,623,102 | 11/1986 | Hough, Jr. . |
| 4,750,492 | 6/1988 | Jacobs ..................... 606/232 |
| 4,866,818 | 9/1989 | Thompson . |
| 4,969,892 | 11/1990 | Burton et al. . |
| 4,976,722 | 12/1990 | Failla . |
| 5,078,731 | 1/1992 | Hayhurst . |
| 5,160,339 | 11/1992 | Chen et al. . |
| 5,171,251 | 12/1992 | Bregen et al. . |

FOREIGN PATENT DOCUMENTS 0490411  6/1992  European Pat. Off. .

OTHER PUBLICATIONS

Schaefer, M. D., et al., *Absorbable Ligating Clips*, Surgery, Gynecology & Obstetrics, vol. 154, pp. 513–516, (Apr. 1982).

*Primary Examiner*—Stephen C. Pellegrino
*Assistant Examiner*—Gary Jackson

[57] ABSTRACT

A suture holding clip including legs each having a suture contacting surface. The legs can be closed to define an interface for holding a suture in a serpentine configuration. In another embodiment the suture holding clip is initially in a spider leg configuration with a spine and legs projecting from the spine and alternately angled to one or the other of two directions so as to define therebetween a lengthwise extending passage for the reception therethrough of a suture.

1 Claim, 8 Drawing Sheets

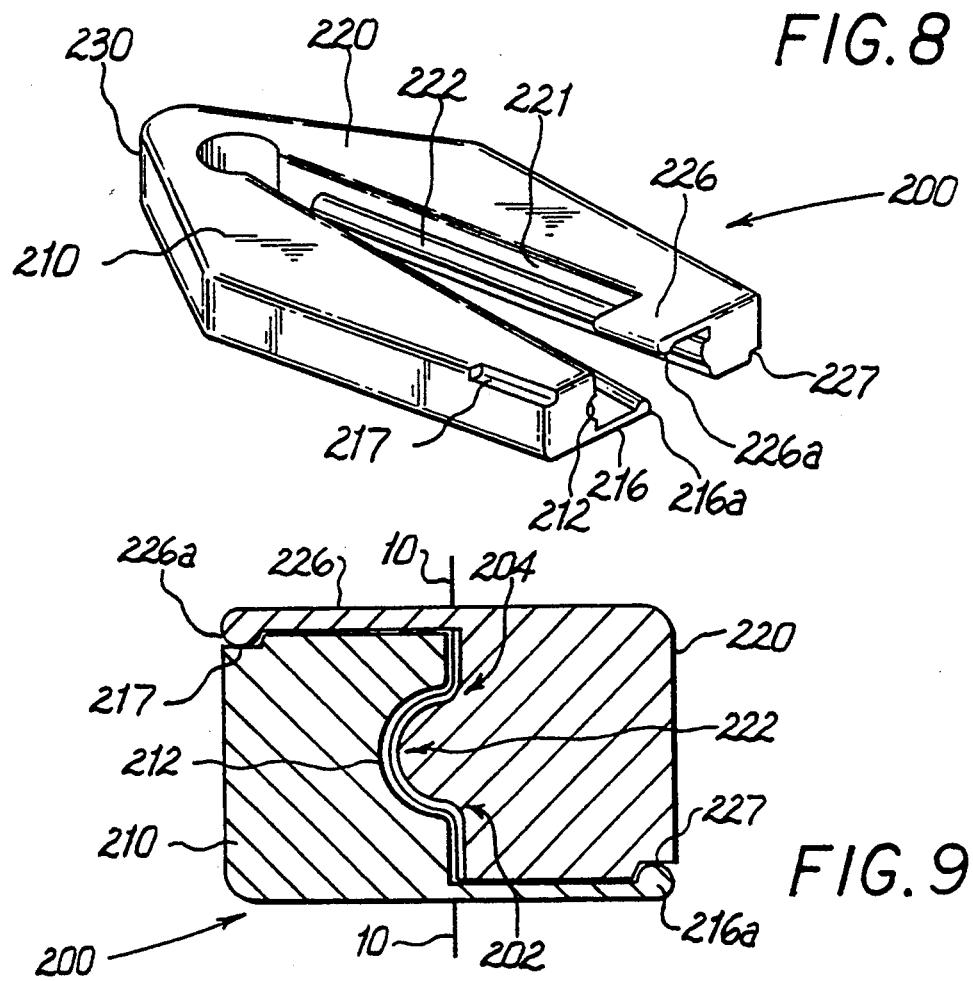
FIG.8
FIG.9
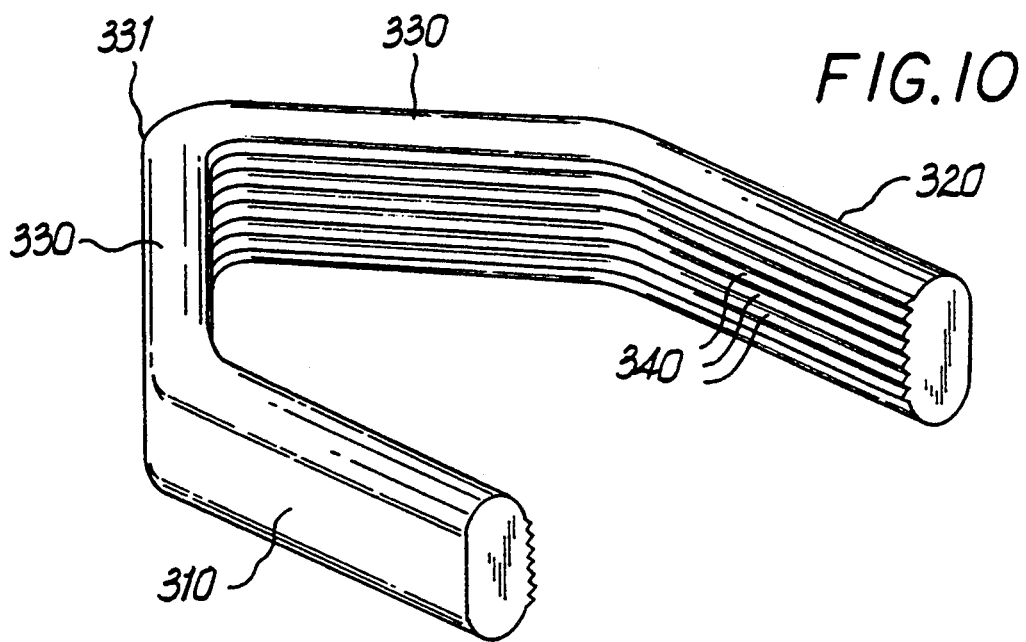
FIG.10

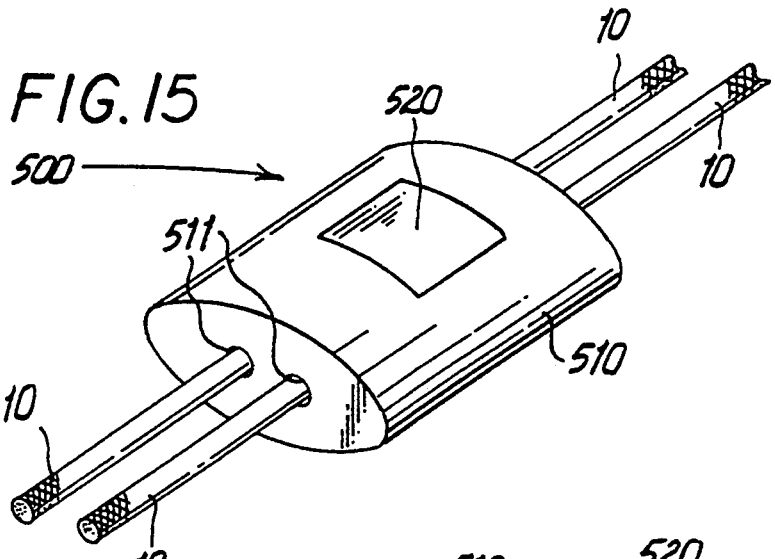
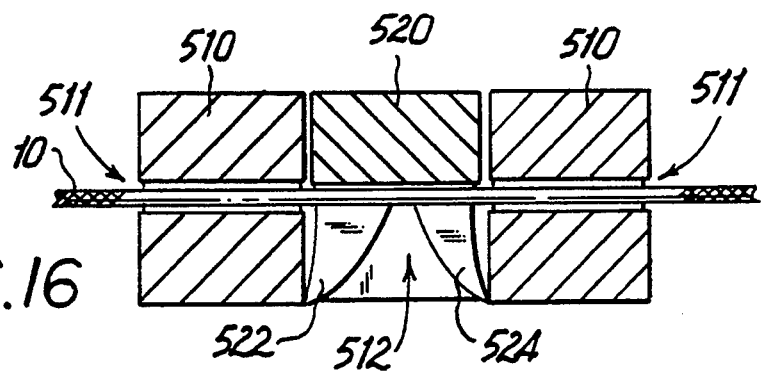
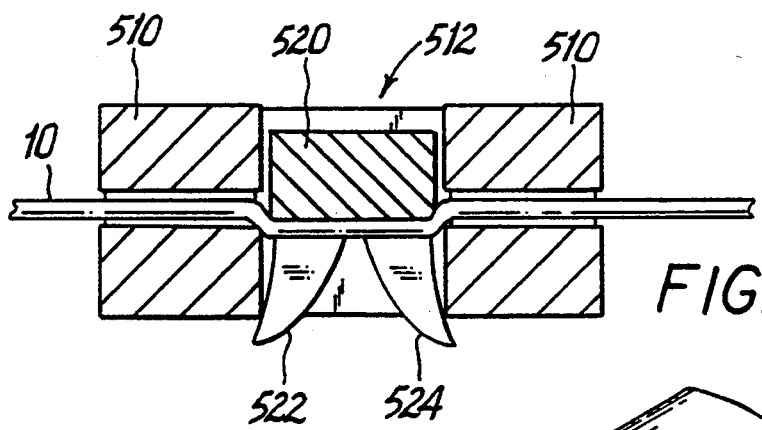
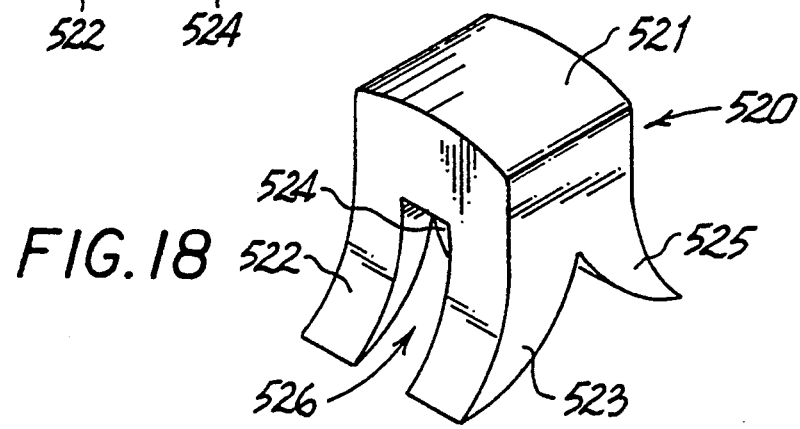

SUTURE RETAINING CLIP

This is a divisional of copending application Ser. No. 07/959,182 filed Oct. 9, 1992.

BACKGROUND OF THE INVENTION

1. Field of the Invention

The present invention relates to a fastening device for use in surgical procedures to secure a suture.

2. Background of the Art

Sutures are commonly used to close incisions and to reunite damaged tissue. Typically, the sutures are passed through the tissue and the free ends of the sutures are tied together. In many instances, the suturing site is exposed to an extent sufficient to permit the surgeon to quickly tie the suture by hand. However, in some procedures such as arthroscopic, laparoscopic or endoscopic surgery, the suturing site is inaccessible by hand. As a result, the surgeon is usually required to tie the suture ends into a knot at a location remote from the suture site, and then manipulate suitably configured instruments for sliding the knot to the site.

For example, arthroscopic surgical procedures usually employ a small diameter cannula that extends through a small incision made in a joint. The sutures extend from the suturing site through the cannula. The exposed free ends of the sutures are tied by the surgeon and the knot is slid through the cannula to the suturing site.

Likewise, laparoscopic or endoscopic surgery also relies on small diameter cannulas inserted through small incisions in body tissue to gain access to the interior of the body. The operating instruments have relatively long and narrow portions which are inserted through a cannula to perform the operation in the interior of the body. The instrumentation for such procedures is actuated from outside the body. It can readily be understood that the dexterity required to free suture ends under such conditions not only places a burden upon the operating personnel, but also poses a greater risk to the patient.

Various devices are known which attempt to deal with the aforementioned problem.

For example, U.S. Pat. No. 4,078,731 to Hayhurst discloses a suture clip for engaging one or more suture thread lines. The Hayhurst suture clip, in an open position, is slidable along the suture(s). When positioned at the suturing site, the Hayhurst clip may then be closed to fix the position of the clip, thereby securing the suture(s).

U.S. Pat. No. 4,291,698 to Fuchs et al. discloses a button type suture retainer including a disk having a slot which extends to a passage for guiding a suture thread therethrough within the circumference of the disk. The passage is sealed by a clamping device for clamping a thread in the passage. The clamping device includes a disk segment movable parallel with the disk over the slot and passage to a latched position where its inner marginal part is past the passage, thereby bending the thread and holding it by friction and compression.

Other suture fixation devices are disclosed in U.S. Pat. Nos. 3,753,438; 3,857,396; 3,910,281; 3,976,079; 4,387,489; 4,750,492; and 4,969,892.

While the aforementioned devices perform the function of suture retention, there is yet need for an improved suture retainer clip which is simple in construction, easy to apply, and usable in laparoscopic or endoscopic or arthroscopic applications as well as in conventional surgical procedures.

SUMMARY OF THE INVENTION

A suture holding clip is provided herein. The suture holding clip includes first and second legs each having at least one suture contacting surface engageable with the suture contacting surface of the other of said legs to form a serpentine interface therebetween. The first and second legs are movable between an open position wherein the suture contacting surfaces define a gap therebetween for the reception of at least one suture strand and a closed position wherein said suture contacting surfaces are engaged.

The suture holding clip includes a proximal base portion to which the proximal ends of the legs are integrally connected. The suture holding clip can further include means to interlock with the other of said legs to prevent reopening of the suture clip after it has been fully closed, and means to couple one suture clip with another.

The suture holding clip is preferably fabricated as a single piece from a flexible bioabsorbable material.

In another embodiment the suture holding clip includes a "spider leg" configuration, which comprises a lengthwise extending spine having a first side, and a plurality of legs extending from the first side along the lengthwise extent of the spine, the legs being alternately angled laterally to one or the other of two directions such that the legs define a lengthwise passage therebetween for the reception of at least one suture strand. The legs are laterally movable to close the lengthwise passage for holding a suture strand in a serpentine fashion. The legs each define a plane orthogonal to the lengthwise direction of the spine, and the legs collectively define a series of planes spaced apart in the direction of the lengthwise extent of the spine.

Also provided herein is a method for repairing body tissue using the aforementioned suture holding clips.

BRIEF DESCRIPTION OF THE DRAWINGS

FIG. 8 is a perspective view of an alternative embodiment of the suture holding clip;

FIG. 9 is a cross-sectional view showing a suture held by the alterative embodiment;

FIG. 10 is a perspective view of a third embodiment of the suture clip;

FIG. 15 is a perspective view of push button embodiment of the present invention;

FIGS. 16 and 17 are sectional views illustrating, respectively, a suture in the pre-actuated push button clip and a suture held in serpentine fashion in the actuated push button clip;

FIG. 18 is a perspective view of the push actuated suture holding member;

DETAILED DESCRIPTION OF PREFERRED EMBODIMENTS(S)

Figure 1:
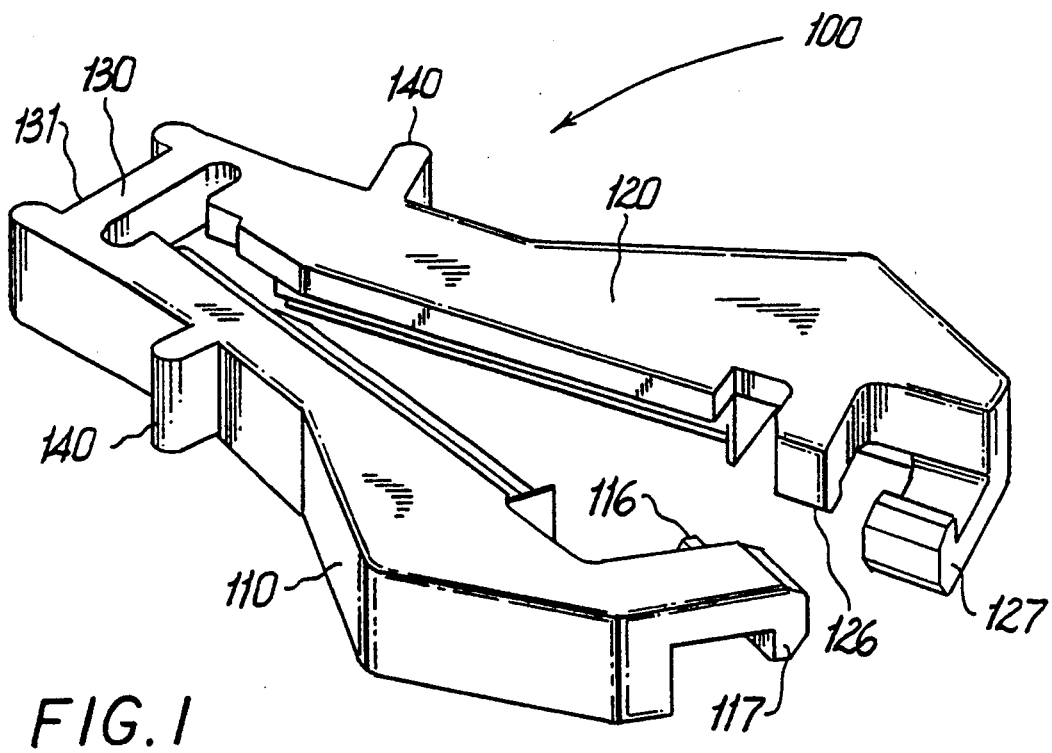
FIGS. 1 and 2 are, respectively, perspective and plan views of a suture holding clip.

Referring to FIGS. 1 to 6, a suture clip 100 is shown. The clip 100 includes a base 130 and two legs 110 and 120 attached to the respective opposite ends of the base 130. The proximal side 131 of base 130 is recessed to receive the pusher of a clip applying device.

Clip applying devices are known in the art and are exemplified in U.S. Pat. Nos. 4,492,232; 4,569,346; 4,557,263; and 4,556,058, all of which are incorporated by reference herein.

Both legs 110 and 120 extend distally from the base 130, and the base and legs collectively define a generally planar configuration. The legs 110 and 120 of each clip 100 initially form equal and opposite obtuse angles with the base 130 of the clips so that the legs are initially spaced apart and diverge from one another in the distal direction. The material and construction of the clip 100 is sufficiently flexible to permit legs 110 and 120 to be brought together into engagement.

Referring to FIGS. 1, 2, 5 and 6, the initially free distal end portion of each arm 110 and 120 includes a proximal latching members 116 and 126, respectively, and distal latching members 117 and 127, respectively. Latching members 116 and 117 respectively overlap and interlock with latching members 126 and 127 to hold the clip closed when legs 110 and 120 are brought together into engagement. It should be noted that the direction of overlap of latching members 116 and 126 is opposite the direction of overlap of latching members 117 and 127. Clip 100, therefore, strongly resists inadvertent reopening even if the arms of the clip are twisted relative to each other.

Figure 2:
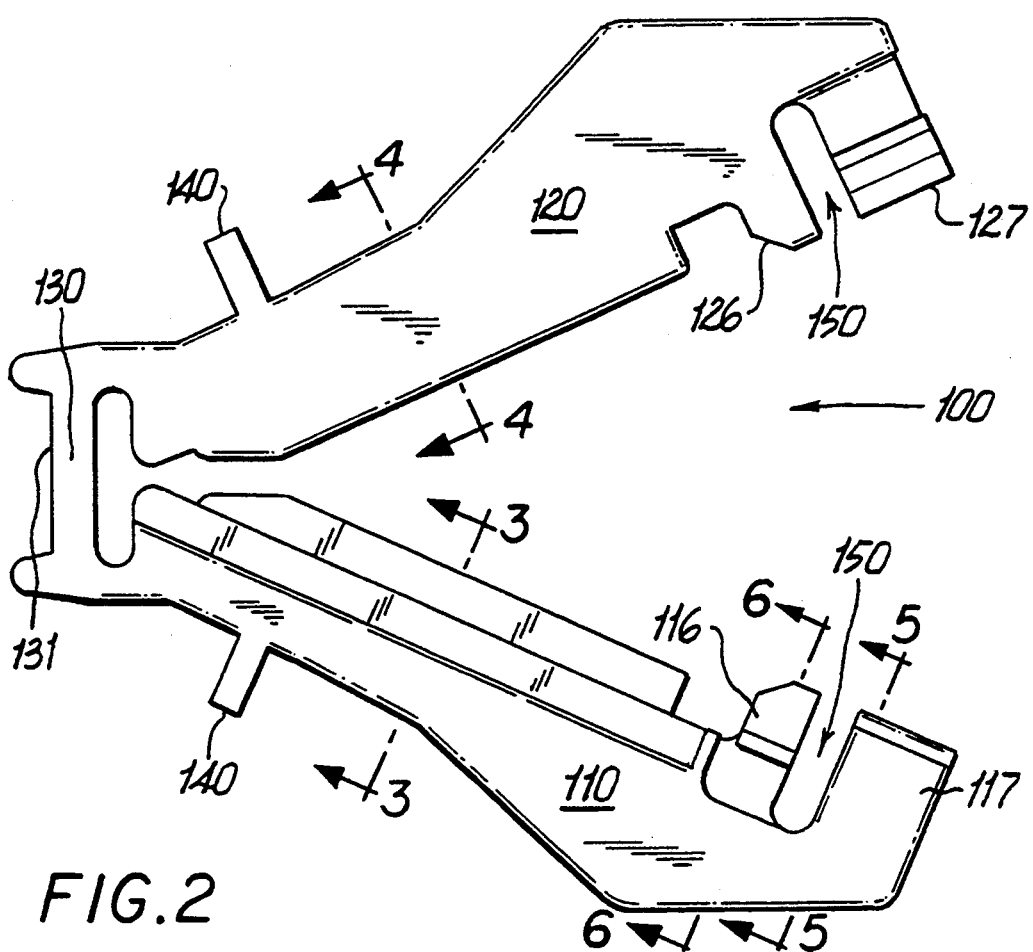

Referring to FIGS. 1 and 2, each clip 100 also includes coupling means 140 and 150 for releasably coupling the physically separate clips together in a linear array or train. The coupling means 140 of each clip releasably couple with the coupling means 150 of the succeeding (i.e., following) clip in the train. Although those skilled in the an will recognize that other coupling means configurations are possible and within the scope of the invention, in the particular embodiment shown, coupling means 140 comprise lugs extending laterally outward from the outer periphery of clip 100, preferably at an intermediate point along the length of legs 110 and 120, and coupling means 150 comprise slots on the inner periphery of legs 110 and 120 near the initially free ends of the legs. When the clips are assembled in a train, the lugs 140 on legs 110 and 120 of each clip respectively project into the slots 150 in legs 110 and 120 of the succeeding clip in the train. Accordingly, all the clips are coupled together so that when the distal-most clip is pushed in the distal direction, each clip pulls along with it the succeeding clip in the train. Thus all the clips move together in the distal direction when the distal-most clip is pushed in that direction.

Clips 100 may have various sizes. Typical clips may be about 10 mm long and 8 mm wide before being closed. The clip applying apparatus is sized appropriately for the clips it is to apply.

Figure 3:
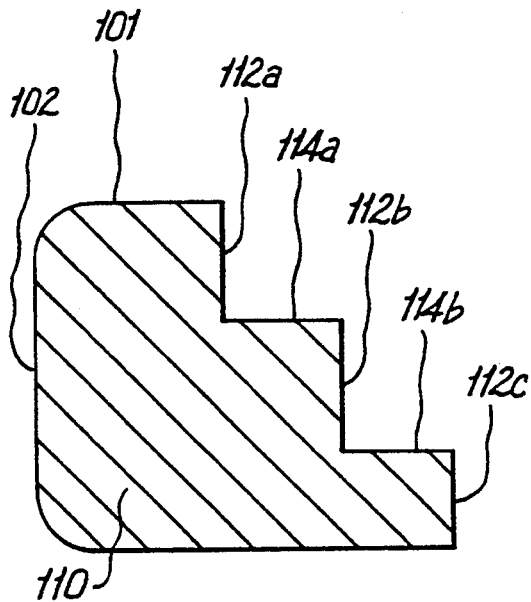
FIGS. 3 and 4 are cross-sectional views illustrating the suture contacting surface of the suture holding clip.
Figure 4:
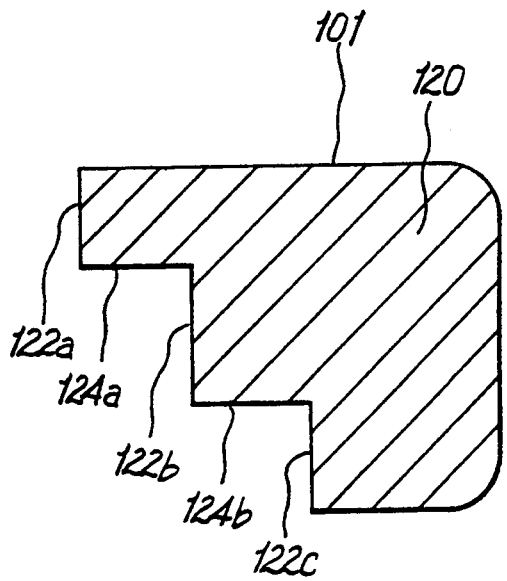
Figure 5:
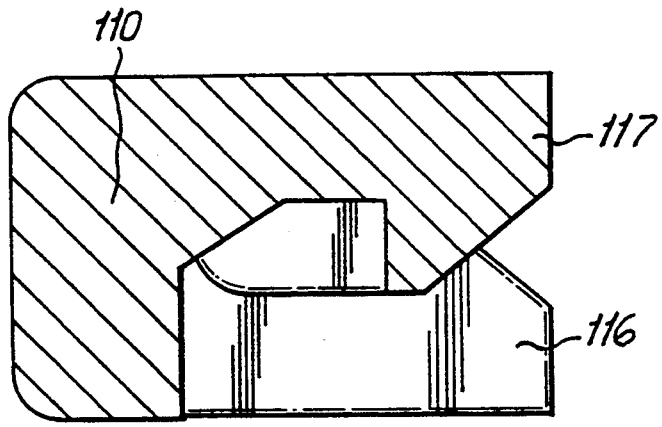
FIGS. 5 and 6 are sectional views illustrating the latch memos of the suture holding clip.
Figure 6:
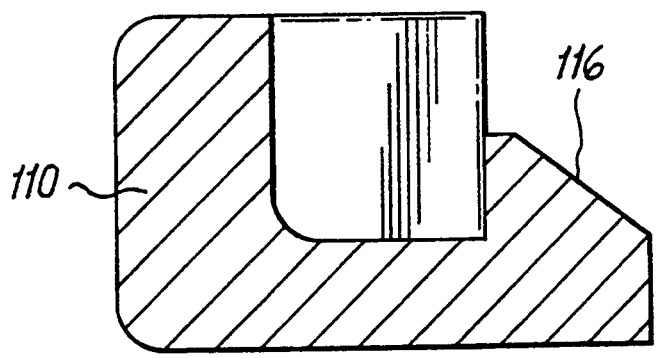

Referring to FIGS. 1, 2, 3, 4, and 7, the suture fastened by clip 100 is held in substantially serpentine fashion, i.e., when the clip is closed on a suture the suture conforms to a configuration in which the suture has at least two distinct bends. As can be seen in FIGS. 3 and 4, arm 110 of clip 100 includes inner surfaces 112a, 112b and 112c oriented generally parallel to side wall 102, and inner surfaces 114a and 114b oriented generally parallel to the top surface 101. Arm 120 includes inner surfaces 122a, 122b and 122c oriented generally parallel to side wall 102 and surfaces 124a and 124b oriented generally parallel to top surface 101. The aforementioned inner surfaces of arms 110 and 120 constitute a suture holding portion of clip 100.

Figure 7:
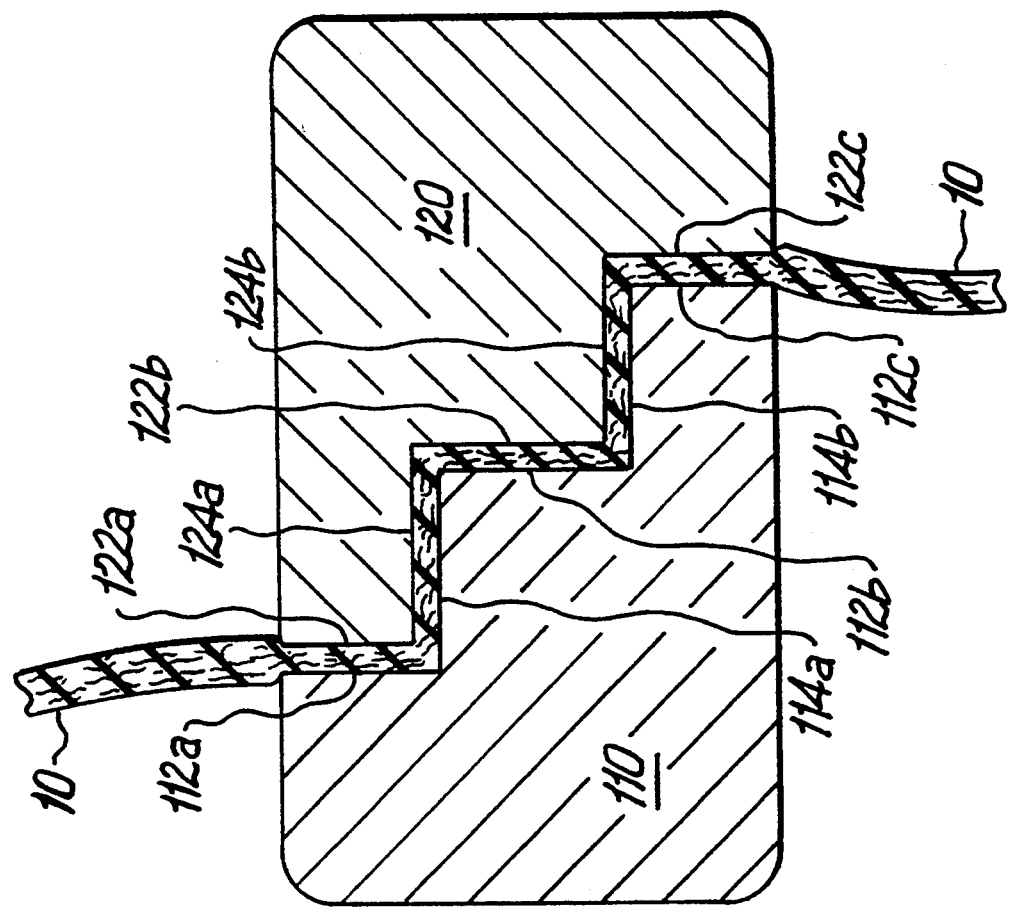
FIG. 7 is a cross-sectional view illustrating a suture held in serpentine fashion by the suture holding clip.

In use, clip 100 is positioned such that a suture extends between the suture holding portions of arms 110 and 120 in a direction transverse to the plane of the clip 100. When the clip is closed, inner surface 112a mates with inner surface 122a (i.e. the surfaces come into close proximity); inner surface 114a mates with inner surface 124a; inner surface 112b mates with inner surface 122b, inner surface 114b mates with inner surface 124b, and inner surface 112c mates with inner surface 112c. FIG. 7 is a cross sectional view showing a suture 10 held in serpentine fashion between arms 110 and 120 of a suture clip 100. Thus, when the clip 100 is closed the inner surface of leg 110 (i.e., 112a, 114a, 112b, 114b, 112c) come into engagement with the respective inner surfaces of leg 120 (i.e., 122a, 124a, 122b, 124b, 122c) to form a substantially serpentine interface. A suture 10 held within closed clip 100 will be conformed to the serpentine interface configuration. As can be seen from FIG. 7, the portion of the suture 10 located between the inner surfaces of legs 110 and 120 has four distinct bends.

Clip 100 may be fabricated as a single price from any biocompatible material suitable for use in surgical application, for example metals and polymers, including bioabsorbable materials such as homopolymers and copolymers of glycolide, lactide, caprolactone, 1,4-dioxanone, trimethylene carbonate, and copolymers and blends thereof.

An alternative embodiment 200 of the present invention is illustrated in FIGS. 8 and 9. Clip 200 is of generally planar configuration and includes legs 210-and 220 connected at proximal end portion 230. Legs 210 and 220 initially are spaced apart and diverge from one another in the distal direction. The material and construction of clip 200 is sufficiently flexible to permit legs 210 and 220 to be brought together into engagement.

The initially free distal end portion of each arm 210 and 220 includes proximal latching members 216 and 226, respectively. Latching members 216 and 226 each include a locking projection, 216a and 226a, respectively. The locking projections 216a and 226a are configured and dimensioned to respectively engage the locking notch 227 and 217 on the opposing leg. Thus, when legs 210 and 220 are brought into a fully closed position, as shown in FIG. 9, latching member 226 overlaps the distal end portion of leg 210 and locking projection 226a snaps into engagement with notch 217 thereby preventing the reopening of the clip 100. At the same time, latching member 216 slides under the distal portion of leg 220 and locking projection 216a snaps into engagement with notch 227, further preventing reopening of the clip 100.

Clip 200 has facing inner suture contacting surface 211 and 221 which are brought into close proximity when the clip is closed. Inner suture contacting surface 221 on leg 210 possesses an elongated detent 212 extending lengthwise thereon. Inner suture contacting surface 221 includes an elongated ridge 222 extending lengthwise thereon. The ridge 222 is adapted to engage detent 212 when the clip 200 is closed.

In use, clip 200 is positioned such that a suture extends between the suture contacting surfaces 211 and 221 in a direction transverse the plane of clip 200. FIG. 9 shows a suture 10 held in substantially serpentine fashion between legs 210 and 220 of suture clip 200. As can be seen from FIG. 9, suture 10 is forced into a configuration wherein it has two bends, one bend at point 202 and another at point 204.

Suture clip 200 can be fabricated as a single piece from any biocompatible material suitable for use in surgical applications such as metals and polymers, including bioabsorbable materials such as homopolymers and copolymers of glycolide, lactide, caprolactone, 1,4-dioxanone, trimethylene carbonate, and blends thereof. The clips of FIGS. 1-9 may be applied by any suitable applier.

Another embodiment of the present invention is illustrated in FIG. 10. Suture clip 300 is a unitary piece comprising two preferably parallel legs 310 and 320 connected by a V-shaped bail portion 330 having an apex 331. The clip 300 includes a plurality of ridges 340 extending lengthwise along the inner surface of the legs 310 and 320 and the bail portion 330, in parallel orientation to each other. Ridges 340 provide means to hold the suture more securely since the suture will be oriented transverse to the ridges 340 when the clip is applied. The suture is not held in serpentine fashion. The clip may be applied by any suitable, e.g. plier-like, applier.

Figure 11:
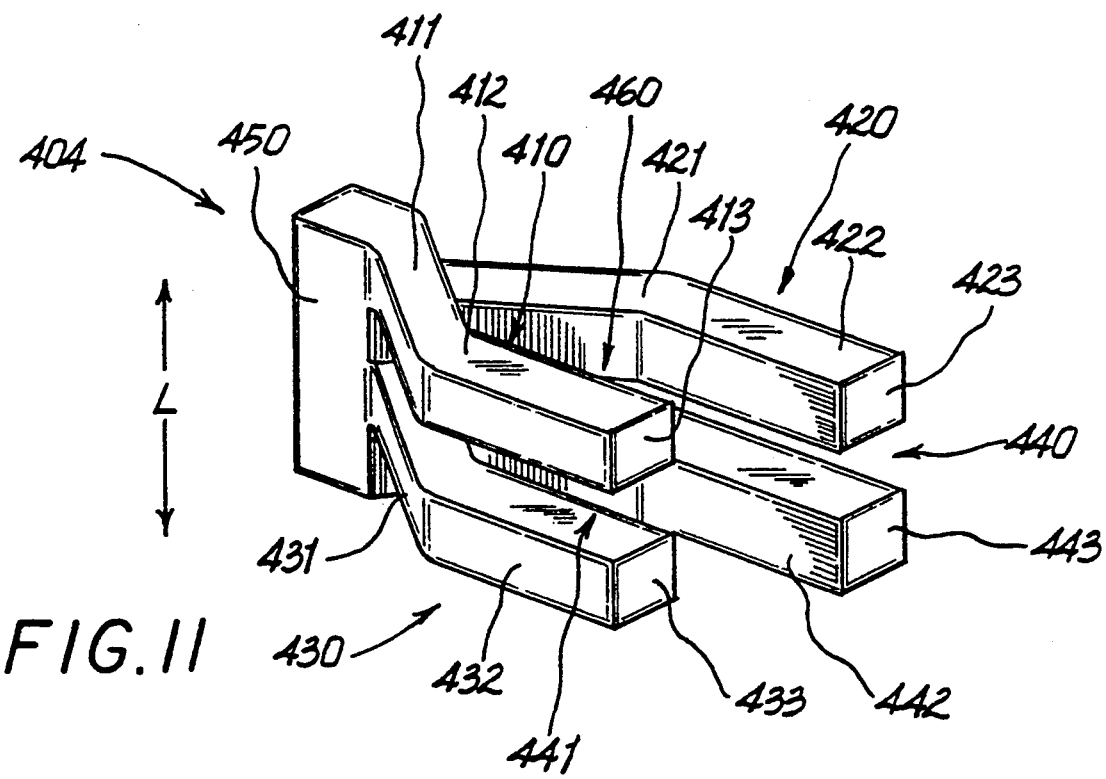
FIGS. 11 and 12 are perspective views of spider-leg embodiments of the suture clip having, respectively, four and three legs.
Figure 12:
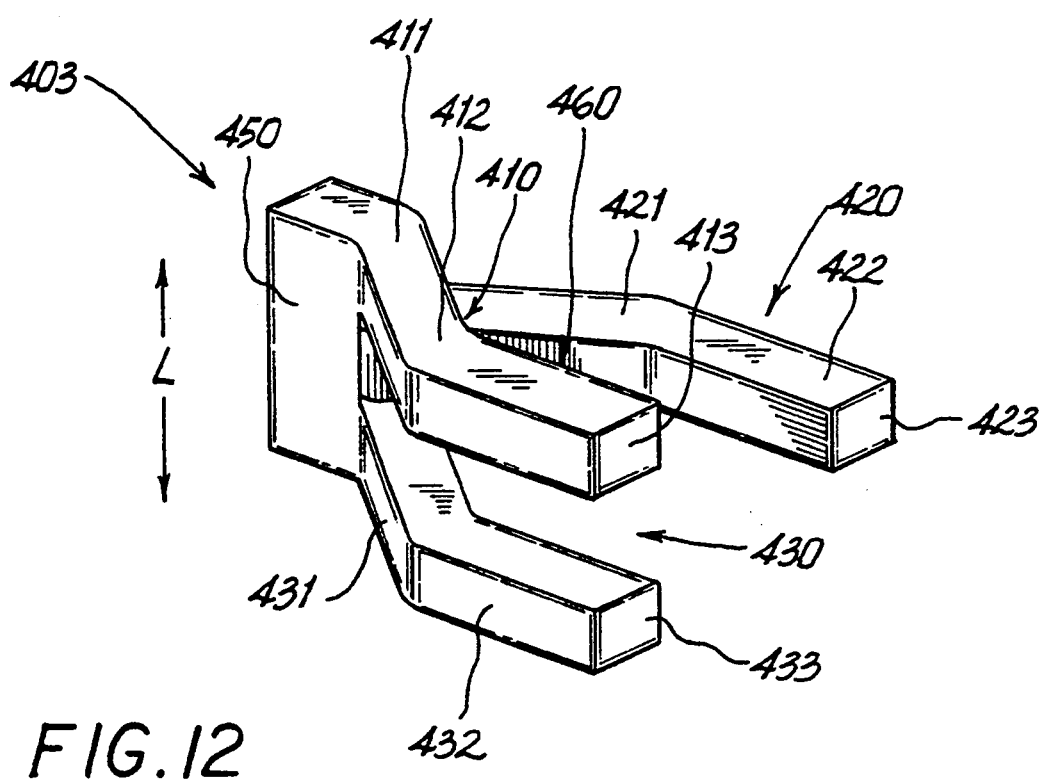

FIGS. 11 and 12 illustrate embodiments of the present invention employing a "spider-leg" configuration to hold a suture in a serpentine fashion. In the spider leg configuration a plurality of legs extend from a side of the spine along a length of the spine. The legs are alternately angled laterally to one to the other of two directions. The angled legs generally define planes orthogonal to the lengthwise direction of the spine. Thus, if the spine were positioned such that it extended lengthwise in a vertical direction, the angled legs would define vertically spaced apart horizontal planes. Since the legs are alternately angled laterally to one or the other of two directions, a lengthwise passageway is defined which can receive a suture. The legs are flexible, and upon the application of a squeezing force are laterally movable toward the alternately angled legs to close the lengthwise passageway thereby holding the suture in a serpentine fashion. Preferably, upon closure the legs are aligned such that the entire clip generally defines a single plane similar, for example, to the arrangement of teeth and spine of a hair comb. FIG. 11 shows a four-leg configuration and FIG. 12 shows a three leg configuration. The operation of the three and four leg embodiments is similar.

Referring now to alternative embodiments 403 and 404, each embodiment includes a backspan 450 of generally rectangular configuration having a lengthwise extension shown by the arrow L. The four-leg embodiment 404 and the three-leg embodiment 403 each have a first leg 410 extending from the spine 450 and having an angled portion 411, and a distal portion 412 having a distal face 413. As can be seen from FIGS. 11 and 12, the direction in which distal portion 410 extends is generally orthogonal to the direction in which spine 450 extends lengthwise. The four-leg embodiment 404 and the three-leg embodiment also each have a second leg 420 extending from the spine 450 and having a distal portion 422 connected to the spine 450 by an angled portion 421. The distal portion 422 has a distal face 423 and is generally parallel to the distal portion 412 of the first leg. Legs 410 and 420 are angled away from each other.

Each embodiment 404 and 403 also each have a third leg 430 extending from the spine 450 and having a distal portion 432 connected to the spine 450 by an angled portion 431. The distal portion 432 has a distal face 433. Third leg 430 is aligned with the first leg 410. The alternately angled legs (i.e., the first and third legs 410 and 430 are angled to one direction and the second leg is angled at an opposite direction) thereby create a passageway 460 therebetween to receive a suture. The four-leg embodiment 404 includes an additional leg 440 extending from spine 450 and having a distal portion 442 connected to the spine 450 by an angled portion 441. The distal portion includes a distal face 443. Fourth leg 440 is aligned with second leg 420 in an angled direction opposite to that of the first and third legs 410 and 430.

Figure 13:
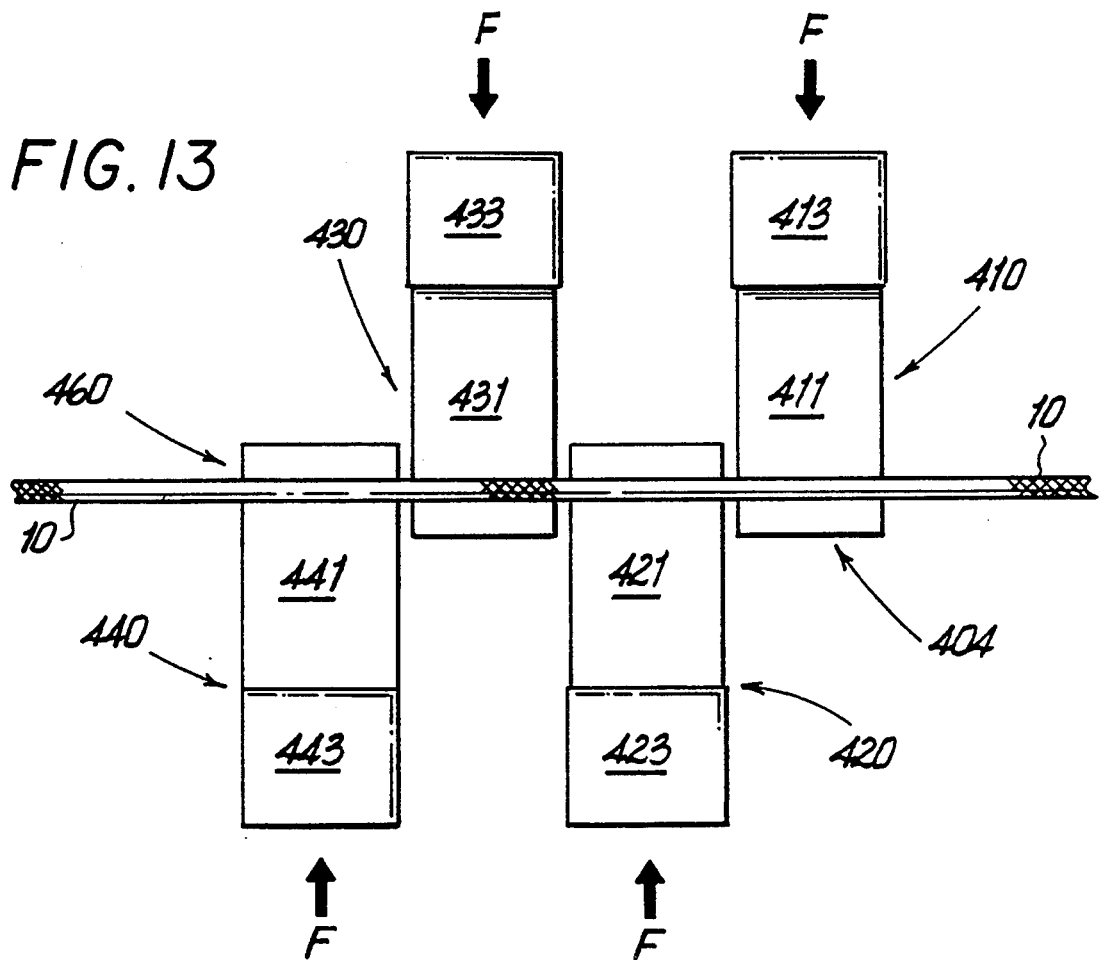
FIG. 13 is a plan view showing a suture placed within an open spider leg clip.
Figure 14:
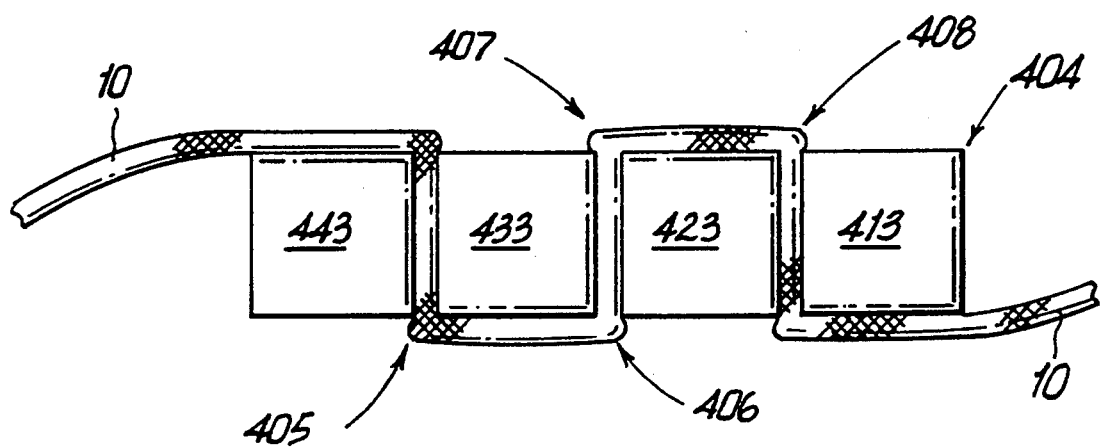
FIG. 14 is a plan view showing a suture held in serpentine fashion within a closed spider leg clip.

FIGS. 13 and 14 illustrate the use of clip 400 for securing a suture. Looking edge on into the open clip, FIG. 13 shows a suture 10 positioned lengthwise in passageway 460 between legs 410 and 430 on one side and legs 420 and 440 on the other. A squeezing force F is applied to the outer surfaces of the legs by any instrument suitable for the purposes described herein (e.g. forceps, or other implements having movable jaws for closing a clip). In response to the applied force, the legs bend inwardly in the direction of the applied force thereby closing passageway 460 and forcing the suture 10 into a substantially serpentine configuration bent at points 405, 406, 407 and 408 as shown in FIG. 14. The suture 10 is thereby securely held by friction and will not easily be pulled out of engagement with clip 404.

The three-legged clip 403 functions in the same way as the four-legged clip 404 except that clip 403 has one less leg.

Alternatively, more than four legs can be embodied in a single clip, although three legs are a minimum for establishing the spider leg configuration of the open clip and serpentine configuration of the fastened suture.

The embodiments of FIGS. 11-14 may be applied by any suitable, e.g. plier-like applier.

The spider leg clips are preferably fabricated as a single-piece from suitable biocompatible materials which are capable of bending into the desired shape. Such materials have been disclosed above in connection with the previously described embodiments herein. Preferably the clips of FIGS. 10-14 are made of metal, more preferably stainless steel or titanium, most preferably titanium.

Referring to FIGS. 15, 16, 17 and 18, a push-button suture holding clip 500 is shown which comprises a body portion 510 having one or more apertures 511 for receiving a suture therethrough. A push actuated suture holding member 520 is slidably disposed through body 510 and has legs 522, 523, 524 and 525 which are resiliently biased to an outwardly curled configuration.

Initially, the suture holding clip is in the configuration shown in FIG. 16 wherein the legs 522, 523, 524 and 525 are substantially completely positioned within chamber 512 of the body 510. A passage for the reception of a suture is defined through suture holding clip 500 by aperture(s) 511 in the body and passageway 526 defined by spaced apart legs 522, 523 and 524, 525 in the suture holding member. A suture 10 may be threaded therethrough.

To secure the suture in serpentine fashion the top surface 521 is pushed or pressed down as shown in FIG. 17. The suture thereby confirms to a serpentine configuration and the ends of legs 522, 523, 524 and 525 are pushed outside of chamber 512 whereupon they resiliently curl to prevent retraction of the suture holding member 500. The suture 10 thus remains securely held. The clip may be held, and top surface 521 pushed, by any suitable means.

In use, a suture is threaded through aperture 511, and clip 500 is slid down along the suture to the desired location at which point surface 521 is pressed to fixedly secure the suture 10. Clip 500 can therefore serve the function of a knot.

Figure 19:
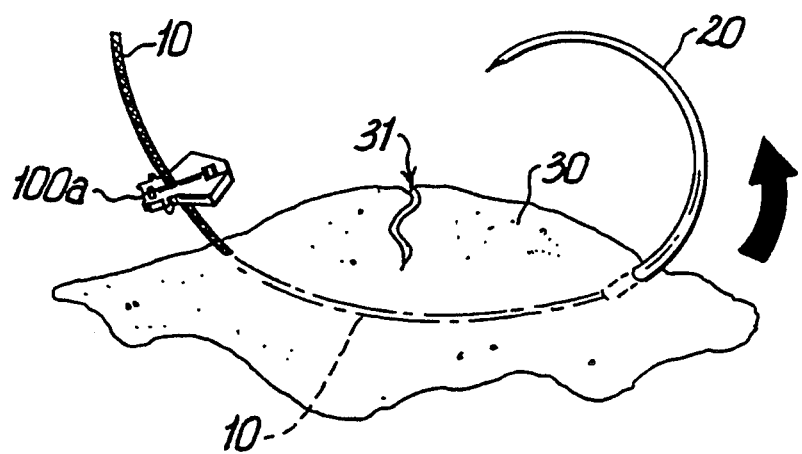
FIGS. 19, 20 and 21 illustrate use of the suture holding clip in a surgical procedure to facilitate the repair of body tissue.
Figure 20:
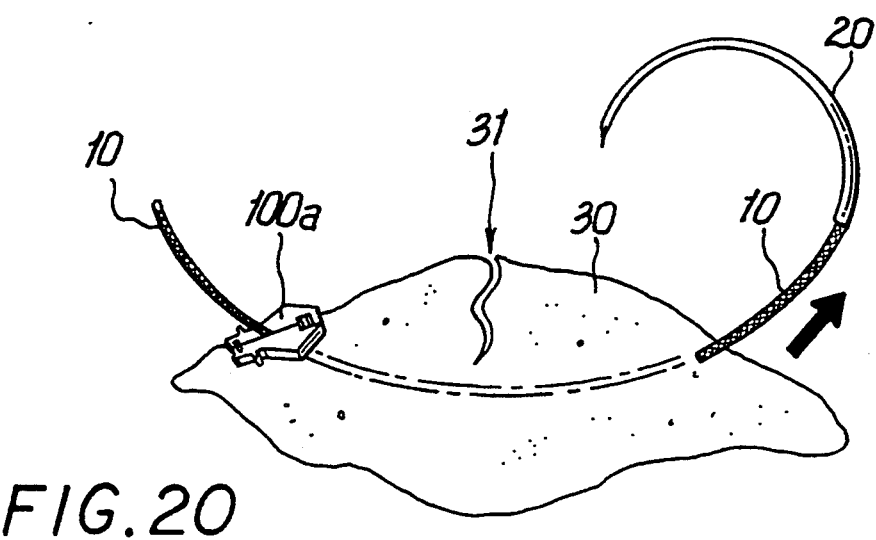
Figure 21:
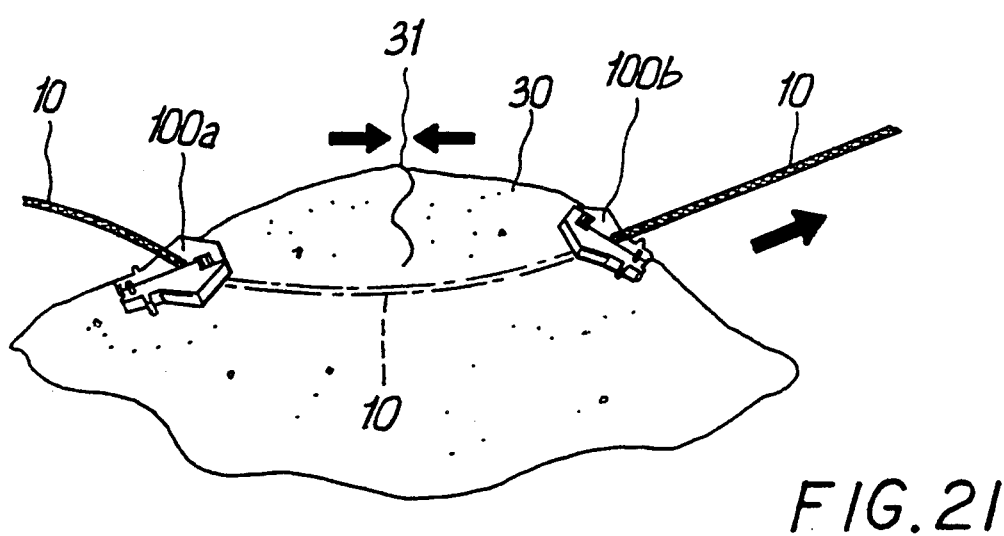

FIGS. 19, 20 and 21 illustrate the employment of the clips described herein in connection with a surgical procedure. Although only clip 100 is illustrated, the procedure described herein is also applicable to clips 200, 300, 403 and 404, as well.

Referring to FIG. 19, body tissue 30 is shown with a gap 31 caused by a tear, incision, or other wound. To close gap 31, the surgeon passed a needle 20 with suture 10 connected thereto through tissue 30 across the tissue gap 31. A first suture clip 100a is applied to a portion of suture 10 extending outside tissue 30 the side of gap 31 opposite to that of needle 20 and, as shown in FIG. 20, the needle-suture combination is pulled until the clip 100 abuts tissue 30. A second clip 100b is positioned in conjunction with the suture at a location on the same side of the gap 31 as that of the needle 20 (i.e. on the side of gap 31 opposite that of clip 100a) and is moved into contact with the tissue 30 with enough force to urge the edges of gap 31 into contiguity. Clip 400b is then fully applied to suture 10 by closing. The gap 31 will remain closed since the clips 400a and 400b bolster the tissue on each side of the gap 31 to prevent separation of the edges of the gap as shown in FIG. 21.

Also, it should be noted that any of the suture holding clips disclosed herein may be used instead of a knot which greatly facilitates a surgical suturing procedure wherein difficult to knot sutures (e.g., monofilament sutures) are employed.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A suture holding clip which comprises:
   a) a body portion having at least one aperture for receiving a suture and a chamber intersecting with said aperture;
   b) a member having a body portion having a top surface plurality of legs extending from a surface of the body portion opposite said top surface resiliently biased to a spread-apart configuration said legs defining a passageway therebetween , said member being slidably disposed within said chamber and movable in a direction transverse to said suture receiving aperture from a first position wherein said legs are located completely within said chamber with said passageway in alignment with said aperture to a second position wherein said legs extend at least partially outside said chamber and are in a spread apart configuration.

* * * * *